United States Patent [19]

Brinkman

[11] Patent Number: 4,808,406

[45] Date of Patent: * Feb. 28, 1989

[54] PREPARATION OF CUPRIC HYDROXIDE COMPOSITIONS

[75] Inventor: Norman C. Brinkman, Houston, Tex.

[73] Assignee: Kocide Chemical Corporation, Houston, Tex.

[ * ] Notice: The portion of the term of this patent subsequent to Dec. 25, 2001 has been disclaimed.

[21] Appl. No.: 901,965

[22] Filed: Aug. 28, 1986

Related U.S. Application Data

[63] Continuation of Ser. No. 678,291, Dec. 5, 1984, abandoned.

[51] Int. Cl.$^4$ .............................................. A01N 59/20
[52] U.S. Cl. ....................................... 424/140; 423/42; 423/43; 423/604; 424/143
[58] Field of Search ......................... 424/140; 423/604

[56] References Cited

U.S. PATENT DOCUMENTS

| Re. 24,324 | 5/1957 | Furness | 23/147 |
|---|---|---|---|
| 1,800,828 | 4/1931 | Furness | 423/604 |
| 1,867,357 | 7/1932 | Furness | 423/604 |
| 2,525,242 | 10/1950 | Rowe | 23/147 |
| 2,666,688 | 11/1954 | Furness | 23/147 |
| 2,924,505 | 2/1960 | Page et al. | 23/14 |
| 3,194,749 | 7/1965 | Furness | 204/96 |
| 3,231,464 | 1/1966 | Dettwiler et al. | 424/140 |
| 3,428,731 | 2/1969 | Furness | 424/140 |
| 3,628,920 | 12/1971 | Barker | 23/315 |
| 3,635,668 | 1/1972 | Barker | 23/147 |
| 4,418,056 | 11/1983 | Gonzales | 424/142 |
| 4,490,337 | 12/1984 | Richardson | 423/604 X |

OTHER PUBLICATIONS

Merck Index—9th ed, 1976, pp. 2631 & 1484.
Butts—"Copper, The Science & Technology of Metal, its Alloys & Cpds", pp. 813–815 (1970).
Mellor-Comprensive Treatise of Inorganic & Theoretical Chemistry, vol. 3, pp. 142–146, 267–268, (1973).

Primary Examiner—Leonard Schenkman
Attorney, Agent, or Firm—Kenneth H. Johnson; Richard L. Moseley

[57] ABSTRACT

A method for producing finely divided stable cupric hydroxide composition of low bulk density comprising contacting solutions of an alkali metal carbonate or bicarbonate and a copper salt, precipitating a basic copper carbonate—basic copper sulfate to a minimum pH in the range of greater than 5 to about 6, contacting the precipitate with an alkali metal hydroxide and converting basic copper sulfate to cupric hydroxide, within the pH range of 7 to 11.

31 Claims, No Drawings

PREPARATION OF CUPRIC HYDROXIDE COMPOSITIONS

This application is a continuation of application Ser. No. 678,291, filed 12-5-84 abandoned.

BACKGROUND OF THE INVENTION

1. Field of the Invention

The present invention relates to a method for producing chemically and color stable cupric hydroxide compositions, suitable for use as a fungicide. In particular, the method employs a class of carbonate compounds as intermediates and may be characterized as carbonate process cupric hydroxide and is an improvement on similar types of processes by providing for control of particle size and bulk density of the resultant product.

2. Related Art

Cupric hydroxide, depending to a large extent on its method of production may not be a stable material. For example, when a base such as sodium hydroxide, is added to a solution of water soluble copper salts, e.g., copper sulfate, a blue, gelatinous precipitate is formed that gradually turns black in color. This material is unstable and contains cupric oxide hydrate and cupric oxide in addition to cupric hydroxide.

U.S. Pat. No. Re 24,324 disclosed a method for the preparation of stable cupric hydroxide. This procedure comprised reacting substantially equal molar amounts of copper sulfate and trisodium phosphate, to obtain a copper containing precipitate. The precipitate is then treated with sodium hydroxide in an amount sufficient to convert a major portion of the precipitate to cupric hydroxide. The sodium hydroxide regenerates the trisodium phosphate. The process is continued by alternately adding copper sulfate and sodium hydroxide. The trisodium phosphate is an intermediate and the alternating additions may be repeated 15 to 20 times in this manner. A solid product is obtained by separating solids, washing and drying the precipitate.

Other methods of preparing phosphate-process cupric hydroxide are disclosed in U.S. Pat. Nos. 2,924,505 and 3,628,920.

A particularly effective fungicidal and bactericidal copper material is disclosed in U.S. Pat. No. 3,428,731 wherein a stable dispersion of phosphate-process cupric hydroxide is obtained in an aqueous medium by having a pH in the range of about 7 to 9.5. This phosphate stabilized cupric hydroxide is suitable for use as a fungicide because of its fine particle size and high surface area, but is not suitable for most industrial applications because of the phosphate ion which has been incorporated in the final product and the resulting insolubles that are found in the reaction medium.

Another approach to producing stable cupric hydroxide is the ammonia-process cupric hydroxide, disclosed in U.S. Pat. Nos. 1,800,828; 1,867,357; 2,525,242; and 3,635,668. These materials are suitable for use as chemical intermediates, however, the individual particles are relatively course and exhibit varying degrees of fungicidal activity. The ammoniacal process also tends to produce cupric hydroxide of higher bulk density and lower surface area than the present method, hence lower reactivity per unit time compared to the present carbonate process cupric hydroxide.

Furthermore, inherent in an ammoniacal process is the problem of further processing the effluent. For example, in the so called "bug ponds" where waste water is treated, ammonia may be a biological poison, which damages the effectiveness of the bacteria in the pond. The ammoniacal process is further complicated in waste water treatment in that ammonia solubilizes the cupric hydroxide to a significant extent, thus further contaminating the waste water with copper and reducing the copper content of the product.

Historically unstable copper hydroxide has been prepared and used in the "Bordeaux" and "Burgundy" mixtures (named for the regions of France where the mixtures were first used as fungicides for grapes). The Bordeaux mixture is obtained by adding copper sulfate to a suspension of hydrated lime. The product is unstable copper hydroxide. The Burgundy mixture is obtained by adding sodium carbonate to a solution of copper sulfate to produce unstable basic copper carbonate ($CuCO_3Cu(OH)_2$).

In commonly owned U.S. Pat. No. 4,490,337 issued Dec. 25, 1984 a carbonate process is disclosed wherein an alkali metal carbonate is reacted with a soluble copper salt and the precipitate (copper carbonate) then treated with alkali hydroxide to convert a major portion of the precipitate to cupric hydroxide. The alkali metal hydroxide regenerates the alkali carbonate. The process is continued by alternately adding copper sulfate and alkali metal hydroxide. The alkali carbonate is an intermediate and alternating the additions may be repeated 15 to 20 times in this manner. In this process the carbonate radical must be preserved to provide the intermediate for the alternating copper reaction and regeneration. The present invention is much simpler in that it is a one step process and the liberation of carbon dioxide from the reaction medium is encouraged and desirable. Furthermore it has been found that the pH range is critical to produce stable cupric hydroxide composition.

The present method has a significant advantage over the related art in that neither ammonia, copper, nor phosphate are introduced into waste water. Another advantage is the presence of carbonate in the waste water, which is a practiced and accepted method of buffering industrial effluents. A feature of the present invention is absence of pollutants in the waste water stream. Another advantage of the present method is the production of much finer particles and much lower bulk density than presently available for similar materials. A further advantage is the use of aqueous dispersions of the carbonate process cupric hydroxide directly as foliage sprays without stickers (adhesive aids, such as starch).

SUMMARY OF THE INVENTION

Briefly, the present invention relates to the method of producing stable cupric hydroxide—cupric carbonate composition which is suitable for use as an agricultural fungicide, and provides a means to control particle size and bulk density of the cupric hydroxide—cupric carbonate product. The present method comprises a process whereby a solution of alkali metal carbonate is reacted with a solution of soluble copper sulfate salt taken to a pH of greater than 5 to about 6 to form an insoluble basic copper carbonate (also called cupric carbonate)—basic copper sulfate intermediate with the evolution of carbon dioxide. The insoluble basic copper carbonate—basic copper sulfate intermediate is then reacted with an alkali metal hydroxide and taken to a pH of 7 to 11 preferably from about 10.0 to about 10.8 (more preferably 10.4 to 10.8) to form insoluble cupric hydroxide—cupric carbonate composition. The reaction is carried on in an aqueous medium. The pH control and alkali metal hydroxide (sodium hydroxide) serve to increase the copper hydroxide ratio in the present composition and to stabilize the azurite (blue copper carbonate) and inhibit its conversion to malachite.

The temperature of reaction would be generally in the range of 5° C. to 32° C. Cupric hydroxide—cupric carbonate composition having bulk density of less than 6 pounds per cubic foot has been produced and particle size of less than 1.0 micrometers and generally larger than 0.5 micrometer average diameter are produced using the present procedure.

DETAILED DESCRIPTION OF THE INVENTION

The alkali metal carbonates include Na, K, Li and Rb, although Na and K are the most preferred because of the availability and ease of use. Some specific soluble carbonates are sodium carbonate, sodium carbonate monohydrate, sodium carbonate decahydrate, sodium carbonate heptahydrate, potassium carbonate, potassium carbonate dihydrate, potassium hydrogen carbonate, potassium carbonate trihydrate, lithium carbonate and rubidium carbonate. Bicarbonate may be employed to generate the carbonate in situ. This is obtained by adding a sufficient amount of an alkali metal hydroxide concurrently with the bicarbonate to produce a pH equivalent to that produced by an amount of carbonate used in place of the bicarbonate, which is substantially about 1 mole of alkali metal hydroxide per mole bicarbonate. Suitable bicarbonates include sodium hydrogen bicarbonate, lithium bicarbonate and rubidium carbonate acid.

The alkali hydroxides are preferably those of sodium, potassium, lithium and rubidium and more preferably sodium and potassium hydroxide.

The various carbonates, bicarbonates and hydroxides can be used with one cation, e.g., sodium or in mixtures.

Any soluble copper sulfate salt such as copper (II) sulfate, copper (II) sulfate pentahydrate, and the like can be employed. Copper (II) sulfate may be conveniently prepared by dissolving copper wire in sulfuric acid.

The process may be carried out by dissolving 1 to 6 moles, preferably about 1 to 3 moles of the alkali metal carbonate or bicarbonate, such as sodium carbonate monohydrate (soda ash) in water. To this solution is added a solution of a 0.5 to 2 molar preferably about 1 to 1.5 molar soluble copper sulfate salt to the pH minimum (pH in the range of greater than 5 to about 6, preferably about 5.3). The molar concentrations are not critical. The insoluble basic copper carbonate—basic copper sulfate intermediate which forms immediately upon addition of the copper salt solution to the carbonate solution is then treated with an aqueous solution of alkali hydroxide such as sodium hydroxide. The total amount of basic solution (alkali hydroxide) which is added depends on the point at which the pH maximum (pH of about 10.8 preferred) is reached. The molar concentration of the alkali metal hydroxide is not critical, however 5 to 6 molar solutions have been found suitable and convenient. The insoluble color-stable cupric hydroxide-cupric carbonate composition is formed.

The solution of soluble copper salt is preferably added such that the molar ratio of copper to carbonate is approximately 0.91:1, whereby an initial curve intermediate is formed which is insoluble and which is immediately precipitated on addition of the copper solution to the carbonate solution. The copper solution may be either dilute or concentrated, however, a concentrated solution is preferred. When copper sulfate is prepared by dissolving copper wire in sulfuric acid the presence of free acid in the copper solution may prevent this amount of copper from being added, since it is the ultimate pH (not less than 5) which controls this step. The alkali hydroxide is preferably added in approximately 0.1–1:1 molar ratio relative to the copper depending on the pH of the solution after the copper solution, again with the pH (10.8 preferred maximum) being the controlling factor.

The order of addition is significant although not critical since the formation of the basic copper carbonate is desired. That is, by adding the copper salt to the alkali metal carbonate the reaction to form carbonate is favored because the reaction system remains basic. The initial pH of the alkali metal carbonate is over 11. The addition of the copper salt will lower the pH. The copper salt is added with stirring until the pH is about 6 (from pH of about 8.5 the evolution of $CO_2$ from the reaction system was observed) and greater than 5, preferably about 5.3. The evolution of $CO_2$ from the reaction system lowers the temperature of the system. Thus keeping the reaction system below a maximum temperature of 32° C. is not a problem, if the temperature of the starting reactant solutions is below about 5° C. To carry the pH to 5 or below in the copper carbonate forming step results in a final product (after alkali metal hydroxide treatment) which is unstable and decomposes (turns dark) before it can be filtered. Thus the lower pH for the carbonate reaction step of the process is above 5, preferably about 5.3.

The reaction products (a light blue precipitate) of the first step are basic copper carbonate and basic copper sulfates. These products are not specific compositions and a great deal of variant speculation exist as to the possible composition of the various copper compounds.

The resultant basic copper carbonate and basic copper sulates need not be recovered and preferably are not for the next step which is the treatment of the basic copper carbonate and basic copper sulfates with an alkali metal hydroxide (caustic) which may convert at least a portion of the copper carbonate and substantially all of the basic copper sulfates to cupric hydroxide. This is achieved by adding a solution of the caustic (alkali metal hydroxide) to the reaction system, preferably in increments with stirring, until the pH is preferably about 10.8. At this pH the conversion of basic copper sulfates to cupric hydroxide is substantially complete, but the conversion of $CuCO_3$ is not complete, which is confirmed by analysis. The weight ratio of cupric hydroxide to cupric carbonate for the present compositions is about 2:1. The cupric hydroxide—cupric carbonate composition of the present invention has slightly less copper than higher purity cupric hydroxide produced by other processes (e.g., 53–57 wt % for the present process versus 58–61 wt % for the phosphate process described above) however, the present material is fungicidally as active as other cupric hydroxides used for that purpose and has bulk density (determined by free fall method) of less than 6 pounds per cubic foot, typically 4 to 5.6 lbs/ft$^3$ and particle sizes of about 0.75 to about 1.0 micrometers, which is about one-half the size of prior cupric hydroxides. These are two major advantages of the present process over other processes. The smaller particle size means that a given quantity of the present cupric hydroxide—cupric carbonate composition will cover approximately twice the plant surface compared to the prior art materials.

When the final pH of the first step is less than 5, it has been observed that the final cupric hydroxide—basic copper carbonate product has much higher bulk density, i.e., above 8 lbs/ft$^3$ and larger particle size, i.e. >1.0 microns.

A proposed mechanism for this result is believed to be that the copper carbonate which first starts forming at approximately pH 8.5 has an ultrafine particle which provides a seeding effect for the formation of very fine particle size basic copper sulfate which is formed later at lower pH. The basic copper sulfate is the material which is later converted to cupric hydroxide, retaining the fine particle size.

If the pH is allowed to go much below 5.3 other species of copper sulfate apparently form which have a much larger particle size. When these basic copper sulfate specie are converted to cupric hydroxide by the addition of the alkali metal hydroxide their larger particles retain the larger size, thereby resulting in cupric hydroxide of higher bulk density and larger particle size than those produced in accordance with the present invention.

As a procedural precaution the alkali metal hydroxide should be added to the precipitated basic copper carbonate basic copper sulfate intermediate as soon as possible, since on standing the blue copper carbonate, azurite, converts to green malachite, which is stable and not a suitable fungicide. Malachite also has greatly increased bulk density and particle size which is undesirable. This conversion is prevented by the alkali metal hydroxide. Thus the alkal metal hydroxide has two functions; (1) to convert basic copper sulfate to cupric hydroxide and (2) stabilize the unchanged basic copper carbonate (cupric carbonate azurite) to prevent it from converting to malachite.

The product may be separated by conventional methods, decantation or vacuum filtration being preferred. The product is washed to remove soluble salts, e.g., sodium sulfate and sodium carbonate salts and is then dried at 60°-70° C. The finished product is found to be comprised approximately of 53-57% copper.

The temperature of the reaction can easily be maintained at less than 32° C. with the reactant's initial temperatures at around 20°-21° C., since the effervescence of the $CO_2$ cools the solution and the alkali metal hydroxide reaction with basic copper carbonate—basic copper sulfate adds only two or three degrees C. to the reaction system. For optimum production efficiency, a more concentrated final slurry of cupric hydroxide—cupric carbonate may be desired and it is found that the copper ion in the copper salt solution of 60 to 90 grams per liter or higher and the hydroxide ion concentration in the alkali metal hydroxide solution of 215 gms per liter (18% solution) or higher is satisfactory. The alkali metal carbonate solution can be made up so that it is near saturation at 20° C.

The water employed may be tap water, deionized water or distilled water. In the present process alkali metal carbonate solution may be added to the copper salt solution, copper salt solution may be added to alkali metal carbonate solution or the two may be simultaneously added to the reaction vessel with the proviso that the final pH of the reaction system is greater than 5, although as stated previously the addition of the copper salt solution to the alkali metal carbonate is preferred.

The chemistry of copper compounds is quite complex as are the resultant compounds. To understand the criticality of the pH ranges the process in its preferred form will be considered. In the present process it is believed that in the first step of contacting copper (II) sulfate with sodium carbonate the cupric carbonate formed corresponds to azurite, $2CuCO_2.Cu(OH)_2$, which on standing converts to malachite, $CuCO_3.Cu(OH)_2$. However, at a pH of between greater than 5 and 6 there is also basic copper sulfate present, which is believed present as mono and dibasic copper sulfate. Below pH 5 there are other species of basic copper sulfate which when reacted with sodium hyroxide produce cupric hydroxide of larger particle size and higher bulk density.

It is one discovery of the present invention that not allowing the pH of the reaction solution to go to 5 or below results in the small particle size and low bulk density of the product after the sodium hydroxide treatment.

It is the basic copper sulfate component of the basic copper—basic copper sulfate which is primarily converted by the sodium hyroxide to cupric hydroxide. The basic copper carbonate remains as such but is stabilized by sodium hydroxide treatment and does not convert to green malachite. The basic copper carbonate is not converted in any substantial quantity to cupric hydroxide until a pH of 13 or greater, however above pH 11 the particle size and bulk density of the resultant product are higher. Thus at pH 11, preferably 10.8 substantially all of the basic copper sulfate is converted to cupric hydroxide which is the most desirable of the copper compounds for use as a fungicide, the bulk density is low and particle size is small. Thus in the present process basic copper carbonate serves as a modifier for obtaining desired bulk density and particle size, which is not obtainable by other processes.

The effectiveness of the copper compounds as fungicides is believed to relate to the leaching of copper from the compounds. For example, copper sulfate leaches quickly and will kill the plants, basic copper carbonate leaches more slowly than the copper sulfate and is used as a fungicide. Cupric hydroxide however, has the best leach rate, giving longer protection without plant damage. The present compositions which contain both cupric hydroxide and basic copper carbonate have substantially the same effect as cupric hydroxide, but at lower copper content because the particles are smaller and cover more plant surface. Hence the dilution of the cupric hydroxide with basic copper carbonate, (azurite) has not been a detriment. An advantage of obtaining fungicidal protection substantially equal to cupric hydroxide but with less copper content is that the rate of copper build up in the soil is reduced, without sacrificing the benefit of the protection from plant fungus. This is particularly beneficial in certain african countries where copper build-up in the soil is becoming a problem.

The x-ray diffraction pattern of the present product is amorphous with essentially indistinguishable peaks as compared to cupric hydroxide or basic copper carbonate which both show sharp clear peaks. Examination by photomicrographs shows cupric hydroxide to have needle like crystals and cupric carbonate (azurite) to have fine grained agglomerates. The present product shows a mixture of needles and fine grained material which distinguishes it from other products of a similar nature.

EXAMPLE 1

To 1786 gallons of water in a 4000 gallon stirred reaction vessel was added 2107 pounds of granulated sodium carbonate, which was stirred until all of the solids dissolved. To this solution was added a solution of $CuSO_4$ equivalent to 80 grams per liter. After approximately 1100 gallons of the copper sulfate solution was added, the pH was about 8.5 and $CO_2$ effervescing was visible. After the addition of 1700 gallons of copper sulfate solution, the pH was accurately measured and addition $CuSO_4$ solution added to lower the pH to 6. A light blue precipitate was observed.

To this system was added about 220 gallons of 18% NaOH in 50 gallon increments with three minutes between additions. The final pH was brought to 10.4 by addition of the NaOH solution.

The slurry was vacuum filtered and washed with about 1700 gallons of water and dried in a continuous belt drier in stages at air temperatures in the range of 100° to 77° C. for about 80 minutes total retention time.

The x-ray powder diffraction data indicated a highly amorphous particle with no sharply defined structure in the spectrum. The dried product contained 55% copper, had a bulk density of 5.7 lbs/ft$^3$ (free fall) and average particle size of 0.8 micron. Particle sizes were measured on a Sedigraph 5000 Particle Size Analyzer (Micrometrics Instrument Corporation, Norcross, Ga.) at 50% cumulative mass level.

Preliminary field tests showed this material to be as effective in a 40% copper content formulation as commercial phosphate process cupric hydroxide with a 50% copper content formulation.

EXAMPLE 2

Several runs were made using the same reactants. The quantities and product results are reported in the Table. 192 ml of 1.3M $Na_2CO_3$ was placed in the reaction vessel. To this was added with stirring copper (II) sulfate solution (81.4 gram/liter) until the pH was 5.3. To this reaction mixture a NaOH solution (5–6 molar) was added to obtain the desired final pH. The data indicate the optimum product, Cu content, bulk density and particle size at pH 10.8. Lower final pH product has lower copper content and over pH 10.8 bulk density and particle size begin to increase. Particle size and bulk density were measured as in Example 1.

Based on the analysis, the composition of two products were calculated as shown in the Table. The theoretical composition of malachite (2 $CuCu_3 \cdot Cu(OH)_2$) is $CuCO_3 = 71.70$ wt % and $Cu(OH)_2 = 28.30$ wt. %. It can be seen from the Table that the present products have different composition than azurite.

TABLE

| Run | pH after $CuSO_4$ | $CuSO_4$ ml | pH after NaOH | grams product | Bulk Dens lbs/cu ft | Particle size micrometers | PRODUCT COMPOSITION WT % | | | | Calculated wt % | |
|---|---|---|---|---|---|---|---|---|---|---|---|---|
| | | | | | | | Cu | $SO_4$ | C | H | $CuCO_3$ | $Cu(OH)_2$ |
| A | 5.3 | 195 | 10.4 | 29 | 4.0 | 0.83 | 54.1 | 2.3 | 3.73 | 1.35 | | |
| B | 5.3 | 204 | 10.6 | 29.8 | 4.0 | 0.98 | 55.3 | 2.1 | 3.07 | 1.46 | 31.61 | 70.62 |
| C | 5.3 | 207 | 10.8 | 28.4 | 4.0 | 0.83 | 56.3 | 1.7 | 2.96 | 1.46 | 30.45 | 70.62 |
| D | 5.3 | 204 | 11.0 | 28.0 | 4.2 | 0.86 | 56.8 | 1.9 | 2.79 | 1 | | |

The invention claimed is:

1. The method of producing stable cupric hydroxide—cupric carbonate composition comprising the steps of:
    (a) adding a 0.5 to 2 molar aqueous solution of copper sulfate salt to an aqueous solution of 1 to 6 moles of alkali metal carbonate solution thereby forming a precipitate of basic copper carbonate and basic copper sulfate mixture, until the pH of the resulting mixture is in the range of greater than 5 to about 6 with carbon dioxide evolution beginning about pH 8.5;
    (b) adding an aqueous solution of alkali metal hydroxide to the mixture of step (a) to a pH in the range of about 10.0 to about 10.8, to form a solid cupric hydroxide—cupric carbonate composition and
    (c) recovering and drying solid cupric hydroxide—cupric carbonate composition, said recovered and dried solid cupric hydroxide—cupric carbonate composition having a particle size of less than 1.0 micrometers.

2. The method according to claim 1 wherein the particle size of the dried cupric hydroxide—cupric carbonate composition is in the range about 0.75 to about 1.0 micrometers and contains from about 53 to 57 weight % copper.

3. The method according to claim 1 wherein the alkali metal for said carbonate and said hydroxide are independently selected from sodium, potassium, lithium or rubidium.

4. The method according to claim 3 wherein said alkali metal is sodium or potassium.

5. The method according to claim 3 wherein the alkai metal is the same for the carbonate and the hydroxide.

6. The method according to claim 1 wherein the copper sulfate salt is copper (II) sulfate.

7. The method according to claim 6 wherein the alkali metal carbonate is sodium carbonate.

8. The method according to claim 7 wherein the alkali hydroxide is sodium hydroxide.

9. The method according to claim 6 wherein said alkali metal carbonate is potassium carbonate.

10. The method according to claim 9 wherein said alkali metal hydroxide is potassium hydroxide.

11. The method according to claim 1 wherein the alkali metal carbonate is sodium carbonate.

12. The method according to claim 1 wherein the alkali metal hydroxide is sodium hydroxide.

13. The method according to claim 1 wherein from 1 to 3 moles of alkali metal carbonate are present in said aqueous solution.

14. The method according to claim 1 wherein the solution of copper sulfate salt is added until the pH of the resulting mixture is about 5.3.

15. The method according to claim 1 wherein the temperature of steps (a) and (b) is maintained below 32°C.

16. A composition of matter produced according to the process of claim 1 having a particle size in the range of about 0.75 to about 1.0 micrometers and contains from about 53 to 57 weight % copper for use as an agricultural fungicide.

17. The method according to claim 1 wherein the pH in step (b) is in the range of about 10.4 to about 10.8.

18. The method according to claim 1 wherein the particle size of the dried cupric hydroxide—cupric carbonate composition is in the range of about 0.75 to about 1.0 micrometers.

19. The method according to claim 1 wherein particle size of the dried cupric hydroxide—cupric carbonate composition is larger than 0.5 micrometers.

20. The method according to claim 1 wherein the alkali metal hydroxide of step (b) is about a 5 to 6 molar solution.

21. The method according to claim 1 wherein the added alkali metal hydroxide of step (b) is in the range of about 0.1 to 1:1 molar ratio of alkali metal hydroxide:copper.

22. The method according to claim 1 wherein copper sulfate is added to provide a molar ratio of copper to carbonate of about 0.9:1.

23. The method according to claim 1 wherein the temperature in steps (a) and (b) is in the range of 5° C. to 32° C.

24. The method according to claim 1 wherein the alkali metal carbonate is potassium carbonate.

25. The method according to claim 1 wherein the alkali metal hydroxide is potassium hydroxide.

26. The method according to claim 1 wherein the alkali metal carbonate is sodium carbonate, sodium carbonate monohyrate, sodium carbonate decahydrate, sodium carbonate heptahydrate, potassium carbonate, potassium carbonate dihydrate, potassium hydrogen carbonate, potassium carbonate trihydrate, lithium carbonate or rubidium carbonate.

27. The method of producing stable cupric hydroxide—cupric carbonate composition comprising the steps of:
(a) adding a 0.5 to 2 molar aqueous solution of copper sulfate to an aqueous solution of 1 to 3 moles of alkali metal carbonate thereby forming a precipitate of basic copper carbonate and basic copper sulfate mixture, until the pH of the resulting mixture is about 5.3;
(b) adding an aqueous solution of about 5 to 6 molar alkali metal hydroxide to the mixture of step (a), in a molar ratio of alkali metal hydroxide:copper in the range of about 0.1 to 1:1, to a pH in the range of about 10.4 to 10.8, to form a solid cupric hydroxide—cupric carbonate composition and
(c) recovering and drying solid cupric hydroxide—cupric carbonate composition, having a particle size of at least 0.5 and less than 1.0 micrometers; the temperature of steps (a) and (b) being maintained below 32° C.

28. The method according to claim 27 wherein said alkali metal is sodium.

29. The method according to claim 28 wherein the molar ratio of copper to carbonate is about 0.9:1.

30. The method according to claim 27 wherein the temperature in steps (a) and (b) is in the range of 5° C. to 32° C.

31. The method according to claim 27 wherein the alkali metal carbonate is sodium carbonate, sodium carbonate monohydrate, sodium carbonate decahydrate, sodium carbonate heptahydrate, potassium carbonate, potassium carbonate dihydrate, potassium hydrogen carbonate, potassium carbonate trihydrate, lithium carbonate or rubidium carbonate.

* * * * *